United States Patent [19]

Elgendy et al.

[11] Patent Number: 5,596,123
[45] Date of Patent: Jan. 21, 1997

[54] BORIC ESTER SYNTHESIS

[75] Inventors: Said M. A. Elgendy, London; John J. Deadman, Sutton; Geeta Patel, London; Donovan S. Green, London; Jehan A. Baban, London; Vijay V. Kakkar, Bickley, all of Great Britain; Goran K. Claeson, Pelham, Mass.

[73] Assignee: Thrombosis Research Institute, London, United Kingdom

[21] Appl. No.: 459,551

[22] Filed: Jun. 2, 1995

Related U.S. Application Data

[63] Continuation of Ser. No. 157,947, Nov. 23, 1993, abandoned.

[30] Foreign Application Priority Data

Nov. 25, 1992 [GB] United Kingdom .................. 9224702

[51] Int. Cl.⁶ .................................................. C07F 5/02
[52] U.S. Cl. .................................. 558/288; 560/7
[58] Field of Search ........................ 568/6, 288; 560/7

[56] References Cited

U.S. PATENT DOCUMENTS 3,093,674  6/1963  Schechter ............................. 558/288

FOREIGN PATENT DOCUMENTS 0212708  4/1988  European Pat. Off. ............... 558/288

OTHER PUBLICATIONS

Rangaishenvi, et al., "Chiral Synthesis via Organoboranes. 30. Facile Synthesis, by the Matteson Asymmetric Homologation Procedure of α–Methyl Boronic Acids Not Available from Asymmetric Hydroboration and Their Conversion into the Corresponding Aldehydes, Ketones, Carboxylic Acids, and Amines of High Enantiomeric Purity", *J. Org. Chem.* 56:3286–3294 (1991).

Midland, et al., "Stereochemistry at the Migration Terminus in the Base–Induced Rearrangement of α–Haloorganoboranes", *Journal of American Chemical Society* 101(1):248–249 (1979).

*Primary Examiner*—James H. Reamer
*Attorney, Agent, or Firm*—Townsend & Townsend & Crew LLP

[57] ABSTRACT

Stable α-substituted boronic esters, e.g. for use in peptide synthesis, are prepared by reacting a substituted alkene of the formula:

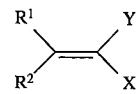

with a disubstituted borane of the formula:

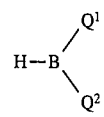

wherein:
(i) $R^1$ and $R^2$ are each selected from various groups which are preferably not leaving groups;
(ii) X is halogen or other leaving group;
(iii) Y is H or lower alkyl;
(iv) $Q^1$ and $Q^2$ are each selected from various groups which are preferably such that the borane is non-hydrolyzable, and particularly $Q^1$ and $Q^2$ together may represent a residue of a diol such as catechol or pinanediol.

20 Claims, No Drawings

BORIC ESTER SYNTHESIS

This is a continuation of application Ser. No. 08/157,947, filed Nov. 23, 1993, now abandoned.

FIELD OF THE INVENTION

This invention relates to the synthesis of boronic esters, more particularly the synthesis of α-substituted boronic esters.

BACKGROUND OF THE INVENTION AND PRIOR ART

α-substituted boronic esters such as α-halo boronic esters are highly promising and useful intermediates in a variety of organic syntheses. They are especially valuable in the synthesis of α-amino boronic esters, as described in Tetrahedron Lett., 1992, 33, 4209–4212, S. Elgendy, J. Deadman, G. Patel, D. Green, N. Chino, C. Goodwin, M. F. Scully, V. V. Kakkar and G. Claeson. These compounds are also useful in the synthesis of peptides, for example as described in published International Patent Application No. WO 92/07869.

A review of uses of α-halo boronic esters is given in Chem. Rev., 1989, 89, 1535–1551, D. S. Matteson.

Hitherto in the literature only two methods have been reported for the direct synthesis of α-halo boronic esters via hydroboration, as described in J. Am. Chem. Soc., 1968, 90, 2915, H. C. Brown and R. L. Sharp.

Firstly, as disclosed in U.S. Pat. No. 3,093,674 (W. H. Schechter), $(MeO)_2BCHClCH_2Cl$ has been synthesized by the reaction of $(MeO)_2BH$ with E-1,2-dichloroethane. The product obtained from the hydrolysis however was contaminated with boric acid, which is corrosive and difficult to remove and therefore reduces the usefulness of the prepared ester in subsequent applications, particularly in peptide synthesis.

Secondly, as disclosed in J. Am. Chem. Soc., 1968, 90 6259–6260, D. J. Pasto, J. Hickman, T-C. Cheng, an alternative method which has been used to prepare α-halo boronic acids is the hydroboration of 1-chloro-2-methyl propene with an equivalent of borane followed by hydrolysis, which yielded (1-chloro-2-methyl propyl) boronic acid. However, if the hydroboration mixture was allowed to stand in THF at room temperature for several hours or if excess $BH_3$, were added, the intermediate α-substituted borane rearranged to isobutyl chloro borane. These reactions are illustrated by the following reaction scheme:

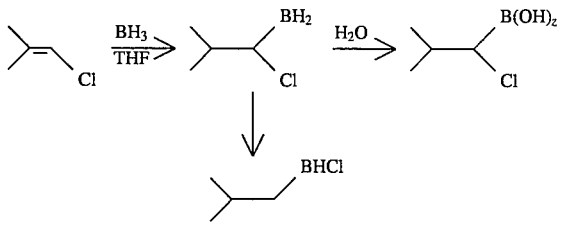

In EP-A-0212708 there are described special catalysts containing rhodium or ruthenium which are useful in the hydroboration (by catecholborane) of various unsaturated hydrocarbon species such as alkenes and alkynes. However, this disclosure is limited to the hydroboration of unsaturated compounds which are unsubstitued.

SUMMARY OF THE INVENTION

Surprisingly, we have now found a novel preparative route to stable α-substituted boronic esters, which solves or at least ameliorates the disadvantages of the prior art preparation methods of these compounds.

Accordingly, in a first aspect the present invention provides a process for preparing a compound of the formula

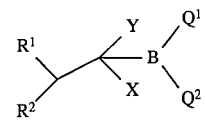

comprising reacting a substituted alkene of the formula

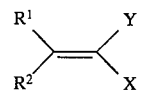

with a disubstituted borane of the formula

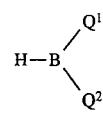

wherein:
(i) $R^1$ and $R^2$ are the same or different and are each independently selected from any of the following groups:
(a) $—(CH_2)_nG^1$
(b) $—(CH_2)_nAr\ G^1$
(c) $—(CH_2)_nG^2Ar$
Where $G^1$ is H, halogen, amino, amidino, imidazole, guanidino or isothioureido; $G^2$ is a linking group derived from an amino, amidino, imidazole, guanidino or isothioureido residue; n in any one or all of (a), (b) and (c) above is an integer of from 0 to 5, preferably from 0 or 1 to 4; Ar is phenyl, thienyl, pyridyl, naphthyl, thionaphthyl, quinolyl, chromenyl, indolyl or wholly or partially (especially in the heterocyclic moiety, if present), saturated groups corresponding to any of these, any of the foregoing groups being optionally substituted with up to 8, preferably up to 5, possibly up to 3, groups selected from $C_1$–$C_3$ alkyl and $C_1$–$C_3$ alkoxy and optionally being bonded to G through a sulphonyl group;
(d) $C_2$–$C_9$ alkyl;
(e) $C_5$–$C_{10}$ aryl or alkylaryl
where any of said alkyl, aryl or alkylaryl groups are optionally substituted with up to 3 groups selected from —OH and $C_2$–$C_4$ alkoxy; or $R^1$ and $R^2$ are as defined above but are linked together to form a cyclic structure;
(ii) X is halogen, preferably Cl, Br, I or F, or other nucleofuge;
(iii) Y is H or an alkyl, preferably $C_1$–$C_4$ alkyl, group; and
(iv) $Q^1$ and $Q^2$ are the same or different and are each independently selected from any of the following groups: halogen; $—OZ^1$; $—NZ^1Z^2$;
where $Z^1$ and $Z^2$ are the same or different and are each independently selected from $C_1$–$C_{10}$ alkyl, $C_5$ or $C_6$ aryl or $C_6$–$C_{10}$ alkylaryl;
or $Q^1$ and $Q^2$ taken together represent a residue of a diol, eg. catechol, pinacol, pinanediol, or dithiol, eg. ethanedithiol.

In certain embodiments of the above process, the identities of $R^1$ and $R^2$ may be such that neither is a leaving group, so that there is site-specific addition of the borane at the 2-position on the alkene. Thus, in such embodiments, when $R^1$ or $R^2$ is $-(CH_2)_nG$ and G is halogen or optionally some other leaving group, then n is not 0.

It may be preferred in certain embodiments that the groups $Q^1$ and $Q^2$ are such that the disubstituted borane is a non-hydrolysable borane, for example certain of those possibilities mentioned above such as $Q^1$ and $Q^2$ together being a catechol or a pinanediol residue.

The above reaction may be readily carried out in the absence of any additional solvent, though it may if desired be carried out in a medium consisting of or comprising an inert solvent, preferably an organic solvent, such as hexane, THF, benzene, toluene, various ethers and other similar solvents known in the art.

Generally the reaction takes place readily at elevated temperatures such as in the range of about 40 to about 120° C., more preferably in the range of from about 60° to about 110° C., even more preferably in the region of about 80° C. The reaction time may be selected as necessary to achieve the desired product yield, and may depend on other reaction parameters such as temperature. By way of example however, reaction times of a few hours up to several, eg. 24 or even 48 hours or more, may be typical. As a general rule, however, the reaction temperature and duration should not be such that there is any or any substantial decomposition of the reactants or product.

Advantageously, the reaction may be carried out whilst irradiating the reacting mixture with ultrasound, in order to induce a faster rate of reaction.

In alternative embodiments of the process of the invention; the above reaction may be readily carried out in accordance with the methods disclosed in, and using the special rhodium or ruthenium-based catalysts described in, EP-A-0212708 mentioned above, the disclosure of which document is incorporated herein by reference.

Typically, in such catalysed reactions the substituted alkene defined above is reacted with catecholborane in an organic solvent (such as those mentioned above) preferably at room temperature (eg. from 15° to 25° C., though temperatures between about 0° C. and 40° C. are possible), in the presence of the catalyst, which is a complex of any of the following formulae:
(i) $RhCl(CO)_x[E(C_6H_5)_3]_{3-x}$
wherein E is arsenic or phosphorus and x is 0 or 1,
(ii) $[RhCl(alkene)_2]_2$
(iii) $[(C_6H_5)_3P]_3 Ru(CO)ClH$ or
(iv) $[(C_6H_5)_3P]_3 RuCl_2$.

The α-substituted boronic esters prepared by the above methods are useful for example as intermediates in the preparation of other boron-containing compounds such as α-amino boronic esters, as referred to hereinabove. The esters may also be useful in the synthesis of peptides, including for example certain of those disclosed in WO 92/07869 referred to above, the disclosure of which publication is incorporated herein by reference. In particular, especially useful intermediates derived from the α-substituted boronic esters prepared in accordance with the present invention are α-substituted boronic acids.

Accordingly, in a second aspect the present invention provides a process for preparing an α-substituted boronic acid, comprising:
(i) preparing an α-substituted boronic ester in accordance with the first aspect of the invention; and (ii) hydrolysing the product of step (i) to form an α-substituted boronic acid of the formula

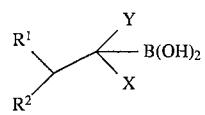

wherein $R^1$, $R^2$, X and Y are as defined above.

The invention will now be illustrated by way of example only by the following Examples.

EXAMPLES

Method A—Hydroboration of 1-halo-1-alkenes (no catalyst)

Experimental procedures

Conventional procedures for the manipulation of boron reagents were followed, as are known in the art. Reactions involving the production of air and water sensitive compounds were carried out under a static pressure of argon or nitrogen directly from the cylinder through a glass line connected via a three-way tap to a vacuum pump. The preparation and purification of reagents for use in these reactions of organoboron compounds were carried out in accordance with well known techniques.

All glassware, syringes, and needles were oven-dried at 140° C. for several hours. The glassware was assembled hot and cooled under a stream of dry nitrogen or argon introduced via hypodermic needles inserted through serum capped inlets with outlets protected by inert oil bubblers. Manipulation of liquids was carried out under an inert atmosphere, using syringes and double-ended needle techniques. Syringes were assembled and fitted with needles while hot and then cooled as assembled units. Unless otherwise stated, the apparatus for reactions at below room temperature consisted of a septum capped flask and a coated magnetic follower to enable stirring of the reaction mixture via an external magnetic stirrer. A bleed needle to the argon line was inserted through the cap to allow for any changes in the pressure within the vessel during reaction. Apparatus for reactions at elevated temperatures consisted of a two-necked round-bottomed flask; one neck equipped with a septum capped tap adaptor, the other with a septum capped reflux condenser carrying a nitrogen bleed.

Preparations

Catecholborane (6 g, 50 mmol) was added dropwise to the 1-halo-1-alkene (50 mmol). The reaction mixture was heated under reflux under argon and monitored by the disappearance of the olefinic protons in the proton NMR. The α-haloboronic ester was obtained by distillation at 90°–120° C./0.05 mmHg in 59–83% yields.

(+) Pinanediol 1-halo alkaneboronic esters were prepared by adding one equivalent of the catecholboronic ester to a solution of (+)-pinanediol in THF.

The reaction mixture was left stirring at room temperature for two hours. The solvent was removed under vacuum and the residue was purified on a column of silica gel (230–400 mesh). Elution with hexane gives the desired products as colourless oils in 85–90% yield.

EXAMPLE 1

(+) Pinanediol-1-bromo propane boronate

Catecholborane (50 mmol) was added dropwise to 1-bromo-1-propene at 80° C. After refluxing the reaction mixture under nitrogen for 24 h, the resulting crude product was treated with a solution of (+) pinanediol (50 mmol, 8.5 g) in THF (20 ml) and the reaction mixture was stirred under nitrogen at room temperature for a further 2 hours.

Solvent was removed under vacuum, the resulting crude product was placed on a column of silica gel (230–400 mesh), eluted with hexane to give the desired product as a colourless oil in 76% yield.

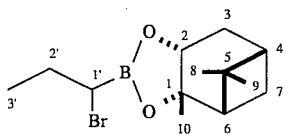

m/z 302 (M+H); $\delta_B$ 31.13; $\delta_H$ 4.34–4.39 (1H, m, H-2), 3.27–3.35(1H, m, H-1'), 2.31–2.45(1H, m, H-3), 2.16–2.3(1H, m, H-7) 2.09(1H, t, J=5 Hz, H-6), 1.91–2.09(2H, H, H-2') 1.81–1.91(1H, m, H-4), 1.69–1.8(1H, m, H-3), 1.41(3H, s, H-10), 1.29(3H, s, H-9), 1.1(3H, t, J=7 Hz, H-3'), 0.8–1.01(1H, m, H-7), 0.85-(3H, s, H-8), $\delta_c$ 86.38(C-1), 78.3(C-2), 51.2(C-6), 39.48(C-4), 38.22(C-5), 35.3(C-3), 28.37(C-10), 27.6(C-2'), 26.9(C-9), 26.2(C-7), 23.94(C-8), 13.41(C-3').

EXAMPLE 2

(+) Pinanediol-1-bromo 2-methyl propane boronate

Catechol-1-bromo 2-methyl propane boronate was prepared by refluxing the catecholborane with one equivalent of 1-bromo-2-methyl propene at 80° C. for 4 hours. The catecholboronic ester product was obtained by distillation of the reaction mixture at 120° C./1 mmHg in 82% yield.

The title compound was prepared by adding one equivalent of the catecholboronic ester to a solution of (+) pinanediol in THF. The reaction mixture was left stirring at room temperature for 2 hours. The solvent was removed and the residue was purified on a column of silica gel, eluted with hexane to give the title compound as a colourless oil in 80% overall yield.

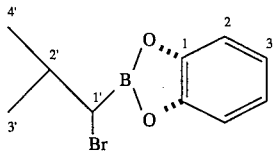

Catechol 1-bromo-2-methylpropylboronate m/z 256 (M+H); $\delta_B$ 32.79; $\delta_H$ 7.02–7.28 (4H, m, Ph), 3.65(1H, d, J=7.2 Hz, H-1'), 2.09–2.35(1H, m, H-2'), 1.11–1.19(6H, q, H-3' & H-4'), $\delta_c$ 147.89(C-1), 123.16(C-2), 112.85(C-3), 31.7(C-2'), 21.38(C-3' & C-4').

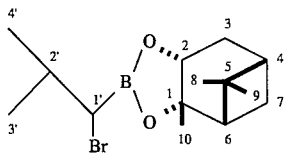

(+) Pinanediol 1-bromo-2-methylpropylboronate m/z 316 (M+H); $\delta_B$ 31.02; $\delta_H$ 4.34–4.39 (1H, m, H-2), 3.41(1H, dd, J=8 Hz & 1.3 Hz, H-1'), 2.23–2.24(1H, m, H-2'), 2.17–2.3(1H, m, H-3), 2.06–2.15(1H, m, H-7), 2.05(1H, t, J=5 Hz, H-6), 1.88–1.99(1H, m, H-4), 1.55–1.8(1H, m, H-3), 1.4(3H, s, H-10), 1.2(3H, s, H-9), 1.03–1.11 (6H, m, H-3' & H-4'), 0.9–1.1(1H, m, H-7), 0.85(3H, s, H-8); $\delta_c$ 86.38(C-1), 78.3(C-2), 51.27(C-6), 39.57(C-4), 38.3(C-5), 35.44(C-3), 31.62(C-2'), 28.44(C-10), 27.01(C-9), 26.2(C-7), 24.02(C-8), 21.52(C-4'), 21.26(C-3').

EXAMPLE 3

(+) Pinanediol-1-bromo 2-phenyl ethane boronate

Catechol-1-bromo-2-phenyl ethane boronate was prepared by irradiating the catecholborane and one equivalent of α-bromostyrene with ultrasound at 50° C.–60° C. for two hours, then, the reaction mixture was left stirring under nitrogen at 60° C. for 18 hours.

A solution of (+)pinadeniol (one equivalent) in THF was added at room temperature and the reaction was stirred for further two hours. The solvent was removed and the unreacted starting material was removed by distillation at 40° C./0.05 mmHg. The residue was placed on a column of silica gel and eluted with hexane to give the desired product as a colourless oil in 59% yield.

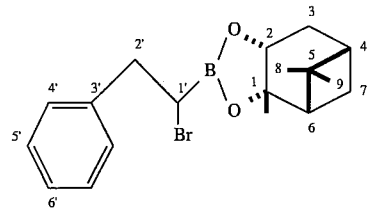

m/z 302 (M+NH$_4$); $\delta_B$ 31.80; $\delta_H$ 7.02–7.42(5H, m, Ph), 4.19–4.31(1H, m, H-2), 3.47–3.56(1H, m, H-1'), 3.1–3.32(2H, m, H-2'), 2.2–2.35(1H, m, H-3), 2.05–2.2(1H, m, H-7), 2.12(1H, t, J=5 Hz, H-6), 1.71–1.95(1H, m, H-4), 1.7–1.75(1H, m, H-3), 1.32(3H, s, H-10), 1.24(3H, s, H-9), 0.95–1.04(1H, m, H-7), 0.78(3H, s, H-8); $\delta_c$ 139.1(C-3'), 129.17(C-5'), 128.24(C-4'), 126.08(C-6'), 86.45(C-1), 78.32(C-2), 51.23(C-6), 40.67(C-2'), 39.23(C-4), 38.21(C-5), 35.16(C-3), 28.27(C-10), 27.09(C-9), 26.37(C-7), 23.96(C-8).

EXAMPLE 4

(+) Pinanediol 1,3-dichloro propylboronate

The named product was prepared by analogous methods as described in Examples 1 to 3, but using 1,3-dichloropropene as the starting alkene and continuing the refluxing for 24 hours, to give the desired product in 79% yield.

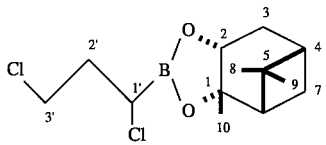

m/z 308 (M+H); $\delta_B$ 31.44; $\delta_K$ 4.2–4.39(1H, m, H-2), 3.71–3.77(2H, m, H-3'), 3.54(1H, t, J=6 Hz, H-1'), 2.35–2.41(1H, m, H-3), 2.25–2.32(2H, m, H-2'), 2.2–2.25(1H, m, H-7), 2.08(1H, t, J=5 Hz, H-6), 1.93–1.99(1H, m, H-4), 1.91–1.93(1H, m, H-3), 1.42(3H, s, H-10), 1.3(3H, s, H-9), 1.01–1.22(1H, m, H-7), 0.84(3H, s, H-8); δ$_c$ 87.05(C-1), 78.74(C-2), 51.31(C-6), 42.12(C-3'), 39.37(C-4), 38.27(C-5), 36.55(C-2'), 35.23(C-3), 28.40(C-10), 27.04(C-9), 26.5(C-7), 23.94(C-8).

EXAMPLE 5

(+) Pinanediol 1-chloro-2-methyl propylboronate

Example 2 was repeated but using 1-chloro-2-methyl propene as the starting alkene and continuing the refluxing for 18 hours.

The final named product was obtained in 66% yield.

EXAMPLE 6

(+) Pinanediol 1,3-dibromo propylboronate

Example 4 was repeated but using 1,3-dibromo propene as the starting alkene and continuing the reflux for only 8 hours.

The final named product was obtained in 76% yield.

Method B-Catalysed hydroboration of 1-halo-1-alkenes by catecholborane

Preparations

Using similar experimental procedures as in the preparations of Method A, the reaction method was carried out according to the following equation:

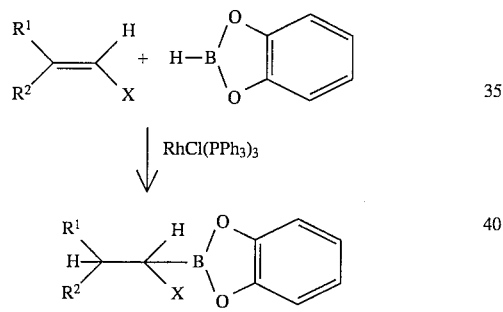

In the presence of Wilkinson's catalyst (0.05–0.5% mol equiv. as indicated in Table 1 below for each Example), catecholborane (45 mmol, 5.4 g) was added dropwise to the appropriate 1-halo-1-alkene (3 mmol) in benzene (5 ml), using conventional techniques for handling air sensitive material, and the mixture refluxed for a period as indicated in Table 1 below for each Example. The reaction mixture was left stirring at room temperature, and monitored by the disappearance of the olefinic protons from the $^1$H nmr spectrum, until the reaction was complete. The desired product was isolated by distillation (using a Kugelrohr distillation apparatus under vacuum) in quantitative yields as indicated in Table 1 below for each Example.

EXAMPLES 7–14

Compounds of the formula:

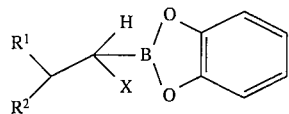

wherein $R^1$, $R^2$ and X have the identities shown in Table 1 below were prepared by the above preparative method using analogous starting materials as for Examples 1 to 6.

TABLE 1

| Example | $R^1$ | $R^2$ | X | Catalyst % | Reaction Time (h) | Isolated Product | % yield |
|---|---|---|---|---|---|---|---|
| 7 | H | H | Br | 0.1 | 36 | (structure) | 73 |
| 8 | Me | H | Br | 0.1 | 8 | (structure) | 82 |
| 9 | CH$_3$(CH$_2$)$_3$ | H | Br | 0.5 | 46 | (structure) | 54 |

TABLE 1-continued

| Example | R[1] | R[2] | X | Catalyst % | Reaction Time (h) | Isolated Product | % yield |
|---|---|---|---|---|---|---|---|
| 10 | Me | Me | Cl | 0.2 | 24 | 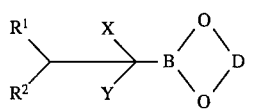 | 70 |
| 11 | Me | Me | Br | 0.05 | 28 | | 98 |
| 12 | ClCH$_2$ | H | Cl | 0.2 | 30 | | 71 |
| 13 | BrCH$_2$ | H | Br | 0.1 | 5 | | 79 |
| 14 | Ph | H | Br | 0.1 | 30 | | 87 |

What is claimed is:

1. A process for preparing a compound of the formula:

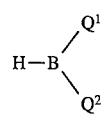

wherein:

(i) R$^1$ and R$^2$ are the same or different and are each independently selected from any of the following groups:
  (a) —(CH$_2$)$_n$G$^1$ where G$^1$ is H or halogen and n is an integer from 1 to 5;
  (b) —(CH$_2$)$_n$Avg$^1$, where G$^1$ is H or halogen and n is an integer from 0 to 5 and Ar is phenyl, thienyl, pyridyl, naphthyl, thionaphthyl, quinolyl, chromenyl, indolyl or wholly saturated groups corresponding to any of these, any of the aforegoing groups optionally being substituted with up to 3 groups selected from C$_1$–C$_3$ alkyl and C$_1$–C$_3$ alkoxy and optionally being bonded to G$^1$ through a sulphonyl group;
  (c) C$_3$–C$_9$ alkyl;
  (d) C$_5$–C$_{10}$ aryl or alkylaryl —where any of said alkyl, aryl or alkylaryl groups are optionally substituted with up to 3 groups selected from —OH and C$_1$–C$_4$ alkoxy; or R$^1$ and R$^2$ are as defined above but are linked together to form a cyclic structure;

(ii) X is halogen or other leaving group;
(iii) Y is H or an alkyl group; and
(iv) —O—D—O— is the residue of a diol or dithiol, the process comprising reacting a substituted alkene of the formula

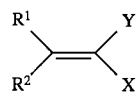

where R$^1$, R$^2$, X and Y are as defined above, with a disubstituted borane of the formula wherein Q$^1$ and Q$^2$ together form the residue of a diol or dithiol, the substituted alkene and disubstituted borane being reacted at a temperature of at least 60° C. or in the presence of a catalyst which is a complex of any of the following formulae:

(i) RhCl (CO)$_x$[E(C$_6$H$_5$)$_3$]$_{3-x}$,
  wherein E is arsenic or phosphorus and x is 0 or 1,
(ii) [RhCl (alkene)$_2$]$_2$
(iii) [(C$_6$H$_5$)$_3$P]$_3$Ru(CO)ClH or
(iv) [(C$_6$H$_5$)$_3$P]$_3$RuCl$_2$.

2. The process according to claim 1, wherein in the formula of the alkene R$^1$ or R$^2$ is —(CH$_2$)$_n$G and G is halogen.

3. The process according to claim 1, wherein Q$^1$ and Q$^2$ represent the residue of catechol, pinacol or pinanediol.

4. The process according to claim 1, wherein the substituted alkene is reacted with the disubstituted borane in the absence of an inert solvent.

5. The process according to claim 1, wherein the substituted alkene is reacted with the disubstituted borane in the absence of a solvent.

6. The process according to claim 1, wherein the reaction is carried out at a temperature at which there is substantially no decomposition of the reactants and the product.

7. The process according to claim 1, wherein the reaction temperature is in the range 60° to 110° C.

8. The process according to claim 1, wherein the reaction is carried out under irradiation with ultrasound.

9. An α-substituted boronic ester prepared by the process of claim 1.

10. A process for preparing an α-substituted boronic acid, comprising:

(i) preparing an α-substituted boronic ester in accordance with the process of claim 1; and (ii) hydrolysing the product of step (i) to form an α-substituted boronic acid of the formula

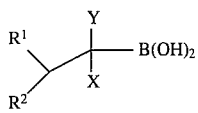

wherein $R^1$, $R^2$, X and Y are as defined above.

11. An α-substituted boronic acid prepared by the process of claim 10.

12. The process according to claim 1, wherein $Q^1$ and $Q^2$ represent the residue of catechol and the process comprises replacing the catechol residue with a pinanediol or pinacol residue.

13. The process according to claim 1, wherein the substituted alkene is reacted with the disubstituted borane under reflux.

14. The process according to claim 3, wherein $Q^1$ and $Q^2$ represent the residue of catechol, the disubstituted borane being catechol-substituted borane.

15. The process according to claim 12, wherein the substituted alkene is reacted with the catechol-substituted borane under reflux.

16. The process according to claim 4, wherein —O—D—O— represents the residue of pinacol or pinanediol.

17. The process according to claim 5, wherein —O—D—O— represents the residue of pinacol or pinanediol.

18. The process according to claim 7, wherein —O—D—O— represents the residue of pinacol or pinanediol.

19. The process according to claim 1, wherein the substituted alkene is reacted with the disubstituted borane under reflux.

20. The process according to claim 12, wherein the substituted alkene is reacted with the catechol-substituted borane under reflux.

* * * * *

UNITED STATES PATENT AND TRADEMARK OFFICE
CERTIFICATE OF CORRECTION

PATENT NO. : 5,596,123
DATED : January 21, 1997
INVENTOR(S) : Said M. A. Elgendy et al It is certified that error appears in the above-indentified patent and that said Letters Patent is hereby corrected as shown below:

On the title page: Item [54] and Column 1, line 2, should read
--BORONIC ESTER SYNTHESIS--.

Signed and Sealed this

Nineteenth Day of August, 1997

*Attest:*

BRUCE LEHMAN

*Attesting Officer*    Commissioner of Patents and Trademarks